United States Patent [19]
Weissman

[11] 4,354,840
[45] * Oct. 19, 1982

[54] SPLINTING DEVICE FOR ANTERIOR TEETH

[75] Inventor: Bernard Weissman, New York, N.Y.

[73] Assignee: IPCO Corporation, White Plains, N.Y.

[*] Notice: The portion of the term of this patent subsequent to Apr. 7, 1998, has been disclaimed.

[21] Appl. No.: 251,774

[22] Filed: Apr. 7, 1981

Related U.S. Application Data

[63] Continuation-in-part of Ser. No. 70,247, Aug. 27, 1979, Pat. No. 4,260,383.

[51] Int. Cl.³ .............................................. A61C 5/00
[52] U.S. Cl. ..................................................... 433/215
[58] Field of Search ................................. 433/215, 225

[56] References Cited
U.S. PATENT DOCUMENTS

| | | | |
|---|---|---|---|
| 4,251,210 | 2/1981 | Weissman | 433/225 |
| 4,251,216 | 2/1981 | Weissman | 433/225 |
| 4,260,383 | 4/1981 | Weissman | 433/225 |

Primary Examiner—Robert Peshock
Attorney, Agent, or Firm—Friedman, Goodman & Teitelbaum

[57] ABSTRACT

A dental splinting device preferably for use in conjunction with at least one anterior tooth. The device includes an elongated bar-like body member having a rear wall, a front wall, and a base wall interconnecting said front and rear wall. Preferably, the front wall has a longitudinally extending portion shorter than the rear wall to thereby define a J-shaped cross sectional configuration. Two tubular members extend perpendicularly from the base wall. A spacer block is provided for receiving the tubular members during the initial drilling of bores in the teeth. Subsequently, the tubular members are inserted directly into the bores formed in the teeth and dental material is placed around the splinting device to retain it in place. In a modified form, pairs of tangentially engaging tubular members extend perpendicularly from the base wall, where one tubular member of each pair may be shorter than the other tubular member thereof.

22 Claims, 23 Drawing Figures

SPLINTING DEVICE FOR ANTERIOR TEETH

RELATIONSHIP TO OTHER APPLICATIONS

This application is a continuation-in-part application of Ser. No. 070,247 filed Aug. 27, 1979, now U.S. Pat. No. 4,260,383 issued Apr. 7, 1981, for "Dental Retaining Splint."

BACKGROUND OF THE INVENTION

This invention relates to dentistry in general, and more particularly to a dental retaining splint for the reinforcement of dentition and especially for use with anterior teeth.

The use of dental splints is a highly specialized field of dentistry. Such splints are utilized for the reinforcement and retention of teeth within the mouth. Most prior art splints and their application have serious limitations, such as the requirement that the securing pins for the splint must be disposed in horizontal parallelism. Other restrictions required the need for involved and complicated procedures in the preparation of the teeth and utilization of special equipment in order to suitably position the splint.

An improved dental retaining splint which avoids such problems was presented in the aforementioned copending parent application and the continuation-in-part of the parent application, now U.S. Pat. No. 4,251,216. The parent application describes a dental retaining splint having an elongated bar-like member with a series of tubular members sequentially extending therefrom.

The tubular members have axial openings extending therethrough. The body member has a substantially H-shaped configuration. The splint is first temporarily held in a channel formed in adjacent teeth with the tubular members extending upwardly from the teeth. The tubular members have axial openings therethrough and such axial openings are used as guides for a drill to form pilot holes in the teeth. The splint is then removed and the pilot holes function as lead holes for the formation of enlarged bores to receive the tubular members therein. The splint is then repositioned so that the tubular members are now disposed downwardly into the bores formed therefor. An inlay fills the channel and covers the splint in the final procedure step.

Accordingly, the dental splint is used both in the formation of the bores in the teeth, as well as for use as the splint itself for insertion into the bores. The dental splint therefore has an upward and a reverse position. One of these positions permits the utilization of the retaining splint as a jig for the drilling of the holes, and subsequently, by inverting the splinting device, it is used in its other position as the actual retaining splint for permanent retention in the teeth.

The particular shape described in the aforementioned copending application has general use within the mouth area. However, it is most convenient for use in posterior teeth, such as the bicuspids and the molars. With these teeth, the occlusal surfaces are wide enough to receive the splinting device. Furthermore, the buccal and lingual heights are substantially the same so that the height of the front and rear walls of the splint can be substantially the same.

A problem, however, arises in connection with the anterior teeth where the labial and lingual surfaces come to a rather sharp incisal tip. As a result, there is sufficient width at the top of these teeth to support the formation of a channel thereacross whereby the channel must be formed at a lower level on these teeth. Furthermore, a channel formed along one of the side surfaces, such as the lingual surface, would provide for a channel having one wall thereof shorter than the other wall, and accordingly, the splint shape of the aforementioned parent application would not be conveniently received in such anterior teeth.

This problem concerning the use of the dental retaining splint in the anterior teeth covers both the right and left central incisors, the lateral incisors, as well as the cuspids. However, another problem exists when desiring to place a dental splint which should span across both the cuspid and the first bicuspid. Although the first bicuspid can receive a channel along its occlusal surface and can receive a splint of the type described in the aforementioned parent application, the adjacent cuspid could not readily receive such splint, and the channel formed therein would not correspond to the channel in the bicuspid. Because of the angled lingual surface of the cuspid, the channel formed therein would have one wall higher than the other wall while the channel formed in the adjacent bicuspid would have both walls of the channel substantially the same height. Therefore, when scanning across teeth extending between the anterior and posterior sections of the dentition, there is again a difficulty in utilizing the specific structure of the dental retaining device of the aforementioned parent application.

Another problem which occurs when using the prior art splints is that frequently it may be desired to have stronger retention of the splint. The individual tubular members may not provide sufficient support in some cases and sturdier support is needed. At the same time, it is still beneficial to utilize the tubular shape for the splint supports since that facilitates the insertion procedure of the splints.

SUMMARY OF THE INVENTION

Accordingly, it is an object of the present invention to provide a dental retaining splint of the type described in the aforementioned parent application and which can be utilized in connection with at least one anterior tooth.

Another object of the present invention is to provide a dental retaining splint which is a modification of the aforementioned dental retaining splint of the parent application.

A further object of the present invention is to provide a dental retaining splint which may be readily secured for the reinforcement and retention of dentition in the mouth and which can be utilized in conjunction with anterior teeth.

Still another object of the present invention is to provide a dental retaining splint which may be fabricated in a simple, efficient and economical manner with the required accuracy for accomplishing the desired ends.

Yet another object of the present invention is to provide a dental splinting device which can be utilized for the formation of aligned bores in the teeth and wherein the device itself serves as the splint.

A further object of the present invention is to provide a procedure for the installation of dental retaining splints in the mouth, and specifically with anterior teeth, with a minimum amount of discomfort to the patient.

Yet another object of the present invention is to provide a dental retaining splint which includes a bar-like body member having tubular members extending perpendicularly therefrom, in conjunction with a spacer block which has aligned bores which can respectively receive the tubular members of the bar-like body member during the formation of bores in the teeth, and whereby the bar-like member with the tubular members can subsequently be utilized as the actual splint itself.

A still further object of the present invention is to provide a dental retaining splint of the type described above which has a substantially J-shaped body member with tubular members extending perpendicularly from the base wall thereof.

Another object of the present invention is to provide a dental retaining splint which utilizes pairs of adjacent tubular members in order to provide extra support for the splint in the teeth.

These objects are achieved in accordance with a preferred embodiment of the present invention, wherein the dental splinting device comprises an elongated bar-like body member having a rear wall, a shortened front wall, and a base wall interconnecting the front and rear walls to thereby define a J-shaped configuration in cross section. At least one tubular member extends perpendicularly from the base wall for being received in a bore provided in a first tooth with the body member being disposed in a channel extending from the first tooth to at least one adjacent tooth, at least one of the teeth being an anterior tooth. Each tubular member includes an axial opening which extends therethrough. The axial opening is utilized for guiding a drill during the formation of a pilot hole in the first tooth. The pilot hole functions as a lead hole for the formation of a bore in the first tooth.

The invention further comtemplates the use of a spacer block having at least one opening therein for receiving the tubular member and securely holding it during the formation of the pilot hole. The height of the spacer block proximates the extended distance of the tubular member from the base wall of the body member.

In the dental procedure, the spacer block is first temporarily held in a channel provided in adjacent teeth in the conventional manner, and the tubular members are inserted into the openings in the spacer block. The tubular members function as guides for a drill to form pilot holes in the teeth. After the pilot holes are formed, the spacer block and the splinting device are removed so that the pilot holes can function as lead holes for the formation of enlarged bores to receive the tubular members therein for retaining adjacent teeth in a fixed position relative to each other. The splint is then replaced in the channel so that the tubular members are disposed in the bores, the higher wall is placed toward the outer face of the teeth, and the shorter wall is placed adjacent the inner face of the teeth. An inlay fills in the channel to cover the splint.

In a further embodiment of the invention there is provided a dental splinting device having an elongated bar-like body member with at least one pair of tubular members extending perpendicularly from the body member and tangentially engaging each other. The pair of tubular members are received in correspondingly engaging bores provided in a first tooth with the body member being disposed in a channel extending from the first tooth to at least one adjacent tooth. Each of the tubular members respectively includes an axial opening extending therethrough for guiding a drill during the formation of a pilot hole in the first tooth. The pilot holes then function as lead holes for the formation of the bores in the first tooth.

The body member can have a substantially U-shaped configuration or alternately a substantially J-shaped configuration, as heretofore described. Furthermore, the body member can be stepped in its longitudinal direction so that one tubular member extends further than the other tubular member.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings, of a preferred embodiment in which.

In the various figures of the drawings, like reference characters desingate like parts.

DETAILED DESCRIPTION OF THE PREFERRED EMBODIMENT

Figure 1:
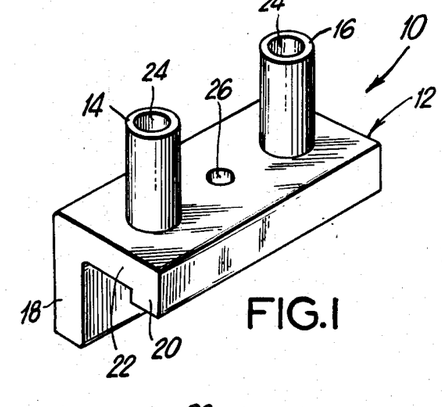
FIG. 1 is a perspective view illustrating a dental splinting device in accordance with the first embodiment of the present invention.
Figure 2:
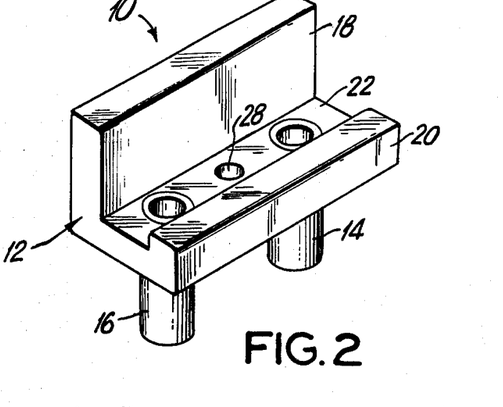
FIG. 2 is a perspective view illustrating the dental splinting device facing in an opposite direction of that shown in FIG. 1.

Referring now to the drawing, FIGS. 1 and 2 show a dental splinting device 10, according to a first embodiment of the present invention. The splinting device 10 comprises a bar-like body member 12 having two tubular members 14, 16, extending perpendicularly outwardly from the body member 12. The dental splinting device 10 can be fabricated from a metal material suitable for use in dentistry so that the splinting device can be disposed in a patient's teeth.

The body member includes a rear wall 18 and a front wall 20 interconnected by a base wall 22. The front wall 20 is shorter or truncated as compared to the rear wall 18 so as to form a channel member having one leg truncated, or preferably described as a J-shaped configuration in cross section.

The tubular members include axial holes 24 extending therethrough. The tubular members extend through the base wall 22 and terminate in the plane of the inside face of the base wall 22.

A set of inwardly extending dimples 26, 28 are opposingly formed on either side of the base wall 22. The dimples are spaced between tubular members 14, 16.

Figure 3:
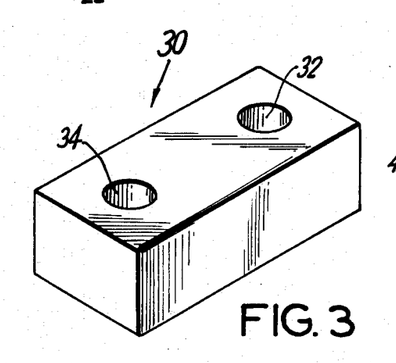
FIG. 3 is a perspective view showing the spacer block which is used in conjunction with the dental splinting device shown in FIGS. 1 and 2.

Referring now to FIG. 3, there is shown a spacer block 30 formed in a substantially rectangular configuration and including spaced part openings 32, 34 extending therethrough. The openings are of a size so as to receive the tubular members 14, 16 of the dental retaining splint 10 of FIGS. 1 and 2 and are aligned so as to securely accommodate the two tubular members. The upper and lower surfaces of the spacer block are proximate the outside surface of the base wall 22 so that the periphery of the spacer block proximates the periphery of the base wall of the splint 10. As a result, when the tubular members 14, 16 are inserted into the receiving openings 32, 34 of the spacer block, the spacer block will appear as a continuation of the base wall 22 of the splinting device.

Figure 4:
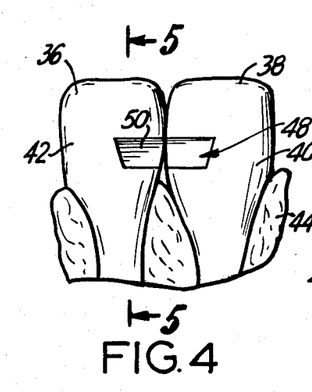
FIG. 4 is a rear view illustrating two adjacent anterior teeth provided with a channel to receive the dental splinting device of the present invention.

Referring now to FIGS. 4-9, the operation of the present inventive device will be described. FIG. 4 shows adjacent anterior teeth 36, 38, such as for example, adjacent central incisors. However, it is understood that also included are the lateral incisors as well as the cuspids. The view shows the lingual surfaces of the teeth 40, 42 downwardly extending into the gum tissue 44.

Figure 5:
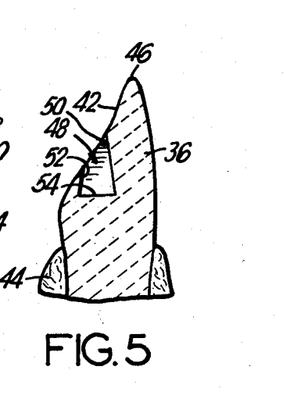
FIG. 5 is a side sectional view taken along line 5—5 of FIG. 4.

As can best be seen from FIG. 5, the lingual surface is an arcuate one angularly descending from the incisal crest 46 toward the gum tissue 44. As a result, a channel 48 which is formed in the lingual surface, includes a front wall 50 which is of greater depth than the rear eall 52. Preferably, as can best be seen in FIGS. 6-8, the walls 50, 52 are tapered to provide a wide base 54 at the bottom of the channel where the tapered walls act to retain the inlay of dental material within the channel as will be explained hereinafter below. The channel 48 is oversized to be larger than the body member of the dental splinting device.

After the channel 48 is formed, a layer of temporary adhesive 56, such as wax or other suitable material, is disposed on the bottom surface or base 54 of the channel. The spacer block 30 is then positioned in the channel 48. Preferably, the splinting device is first inserted into the spacer block by positioning the tubular members 14, 16 into the openings 32, 34, contained in the spacer block, where each of the openings 32, 34 can receive either of the tubular members 14, 16. However, it is also possible to first secure the spacer block in the channel, and subsequently insert the dental splinting device into the already positioned spacer block, where it does not matter whether the spacer block is facing up or down because the upper and lower surfaces of the spacer block are identical.

Figure 6:
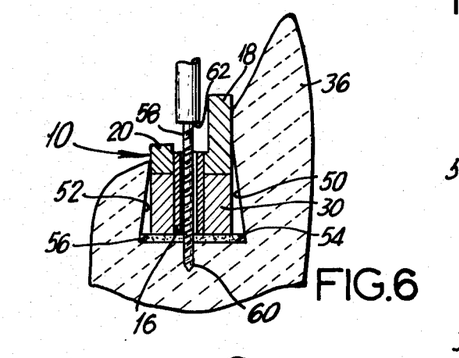
FIG. 6 is an enlarged sectional view, similar to that of FIG. 5, showing the formation of the pilot hole in the teeth with the dental splinting device inserted in the spacer block and using the tubular member of the dental splinting device as the drilling guide.

The height dimension of the spacer block proximates the extended distance of the tubular members from the base wall, as shown in FIG. 6. As a result, with the tubular members inserted into the openings in the spacer block, the distal ends of the tubular members will lie proximately in the same plane as the lower surface of the spacer block.

Once the spacer block and dental splinting device are suitably positioned in the channel 48, as shown in FIG. 6, a pilot drill 58 is inserted into the openings 24 of the tubular members 14, 16, and a pilot hole 60 will be drilled in the respective teeth. Preferably, the drill bit 54 of the pilot drill 58 has a diameter approximately equal to or slightly less than the diameter of the openings 24 of the tubular member so that the tubular members function as guides for the drill bit 58. Furthermore, the drill bit 58 has a predetermined length in order to obtain the desired length of the pilot hole 60. Accordingly, the pilot drill 58 can be provided with a stop or abutment 62 which will contact the upper portion of the tubular members when the desired length of the pilot hole 60 has been reached.

Figure 7:
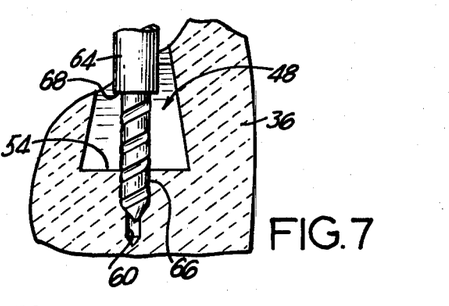
FIG. 7 is a further enlarged side sectional view, similar to that shown in FIGS. 5 and 6, showing the pilot hole functioning as a lead hole for the formation of an enlarged bore in the teeth.

After the pilot holes 60 have been made, the spacer block together with the dental splinting device therein are removed from the channel 48, together with the temporary adhesive 56, as shown in FIG. 7. Another dental drill 64 is now used to form the bores 66 in the teeth, where the pilot holes 60 function as lead holes for the drill bit 64 in the formation of the bores. Here again, the drill bit 64 has a predetermined length in order that the bores 66 have desired selected lengths. The drill 64 can therefore be provided with a stop or abutment 68 which contacts the base 54 of the channel 48 when the desired length of the bores have been reached. The size of the drill bit 64 is such as to be approximately equal, or slightly greater than the outer diameter of the tubular members so as to be able to receive the tubular members therein.

Figure 8:
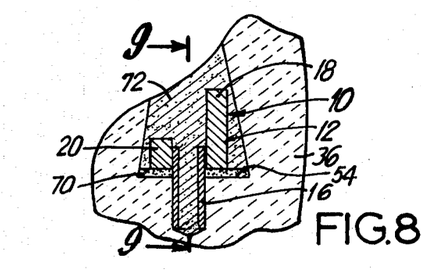
FIG. 8 is a side sectional view, similar to that shown in FIG. 7, showing the dental splinting device permanently secured in the channel of the teeth with the channel being filled with a suitable dental material.
Figure 9:
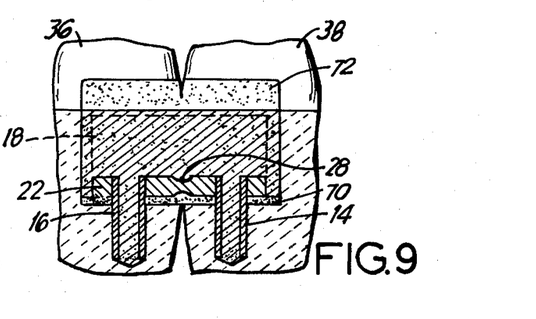
FIG. 9 is a side sectional view taken along line 9—9 of FIG. 8.

A layer of permanent adhesive 70 is then disposed in the bottom surface or base 54 of the channel 48. The dental splinting device is then positioned in the channel with the tubular members 14, 16 disposed in the respective bores 66. An inlay 72 of dental restorative material, such as precious metal, amalgam, composite resin, ceramic, porcelin, or other material is disposed in the channel 48 over the dental splinting device 10, as shown in FIGS. 8 and 9, to cover and complete the dental procedure, where dental inlays are well known in the dentistry art. Thus, the tubular members 14, 16 function to retain the splint 10 in position to secure one tooth to its adjacent tooth, and the tapered walls 50, 52 of the channel 48 retains the inlay 72 in the channel to hold the splints therein.

It should be noted that the J-shaped body member 12 is suitably formed so that the higher leg 18 provides suitable support adjacent to the wall 50 of the channel which is higher than the wall 52 of the channel. The shorter leg 20 of the body member is able to fit against the wall 52 of the channel. If both walls of the body member of the dental splinting device were of the same height, it would either be too short to provide sufficient support for the larger wall 50 of the channel, or would be too large and would extend above the shorter wall 52 of the channel. By means of the particular J-shaped arrangement, the dental splinting device of the present type can be utilized even in conjunction with anterior teeth where the channel will be formed in the curved lingual surfaces of the teeth.

The opposing dimples 26, 28 can be used in certain cases where the length of the channel is such as to require a closer spacing of the drilled bores. In such situation, the dimples can be used to locate the initial starting point for a drill bit and because of the reduced thickness at the point of the dimples, it will be easy for the drill bit to penetrate through the base wall at the point of reduced thickness and continue into the teeth. The use of such dimples as pilot holes has been explained in the aforementioned parent application, all of the subject matter of such parent application being incorporated herein by reference.

Figure 13:
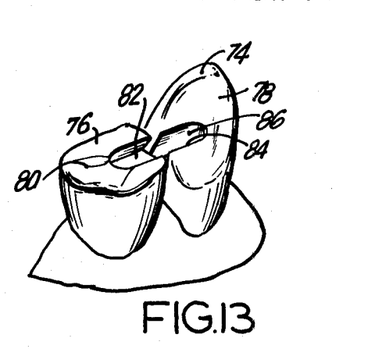
FIG. 13 is a perspective view illustrating adjacent anterior and posterior teeth provided with a channel to receive the dental splinting device shown in FIGS. 10 and 11.

The dental splinting device described heretofore can be used in conjunction with two or more adjacent anterior teeth. However, it is frequently necessary to provide a splinting device between one or more anterior teeth as well as one or more posterior teeth. For example, as shown in FIG. 13, the cuspid 74 is shown with its adjacent first bicuspid 76 of the left upper portion of the mouth. The cuspid 74 again includes the angular lingual surface 78 while the first bicuspid includes the rather flattened occlusal surface 80. A channel 82 formed across the two teeth provides the channel portion in the first bicuspid 76 of the type having front and rear walls of approximately the same height. On the other hand, the channel section formed in the anterior cuspid tooth 74 has one wall 84 which is shorter than the other wall 86.

Accordingly, a splint which would be placed across the adjacent teeth shown in FIG. 13 requires two sections. The first section would necessarily be of the type having a substantially J-shaped cross sectional configuration, of the type shown in FIGS. 1 and 2 of the present application. On the other hand, the splint cross section suitable for the first bicuspid would be a shape closer to a substantially U-shaped cross section.

To accommodate the splinting between such adjacent teeth of the anterior and posterior type, reference is now made to FIGS. 10 and 11, where a suitable dental splinting device will be described. The slinting device is shown generally at 90 and includes a body member 92 having a base wall formed of two adjacent lateral sections 94, 96. The sections are vertically offset from each other to provide a stepped arrangement. Extending from the base wall is a rear wall 98 which has its upper edge 100 lying in a common plane, regardless of the stepped sections.

The front wall 102, on the other hand, has two sections 104, 106 which are vertically offset in a manner corresponding to the offset of the base wall so as to provide a stepped arrangement of the front wall 102. The front and rear walls on section 96 are of the same height, whereas the front and rear walls on section 94 have different heights.

Extending from each section 94, 96 of the base wall is a respective tubular member 108, 110. The tubular members are of approximately the same length so that because of the stepped arrangement, the ends of the tubular members will also be stepped with the tubular member 108 extending outwardly further than the tubular member 110, as shown in FIGS. 10 and 11. The tubular members include axial holes 111 extending therethrough.

Figure 12:
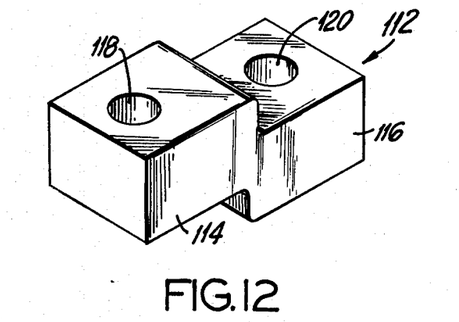
FIG. 12 is a perspective view of a spacer block for use in conjunction with the dental splinting device shown in FIGS. 10 and 11.

In order to accommpodate the stepped arrangement of the dental splinting device, there is provided a stepped spacer block 112, as is shown in FIG. 12. Specifically, the spacer block 112 includes the sections 114, 116 vertically offset from each other to provide a stepped arrangement, as is shown. Each of the sections include an opening 118, 120 extending therethrough of a size so as to respectively receive and retain a tubular member therein. The top and bottm surfaces of the spacer block are identical, so that the spacer block is always right-side up.

Figure 10:
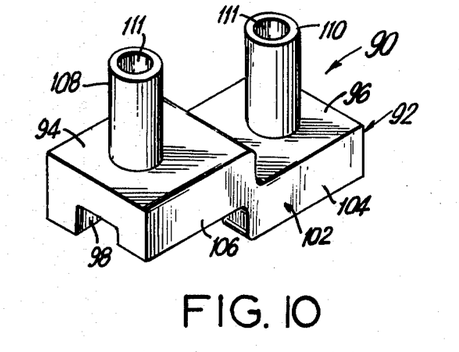
FIG. 10 is a perspective view illustrating another embodiment of the dental splinting device in accordance with the present invention.
Figure 11:
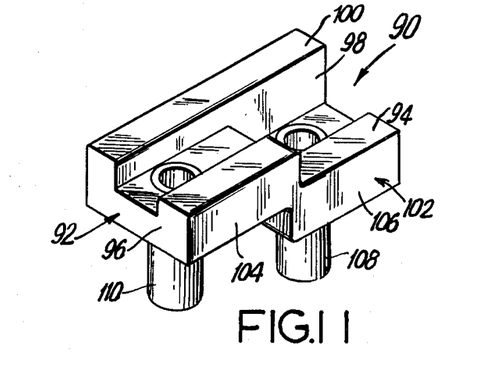
FIG. 11 is another perspective view illustrating the dental splinting device of FIG. 10 facing in an opposite direction thereto.
Figure 14:
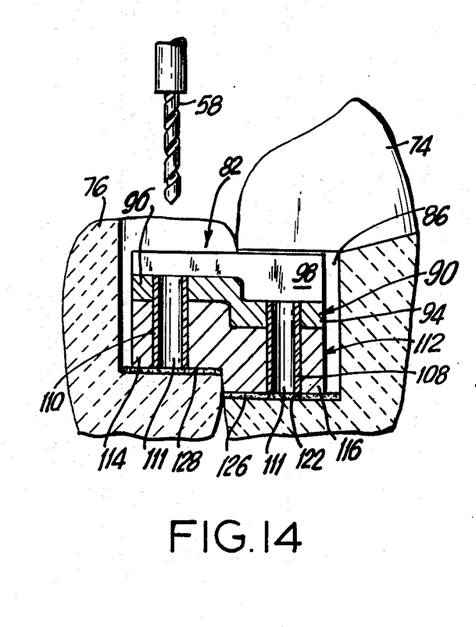
FIG. 14 is an elevational view, partially in cross section, illustrating the formation of the pilot holes in the teeth using the dental splinting device inserted in the spacer block, whereby the tubular members of the dental splinting device are used as drilling guides.
Figure 15:
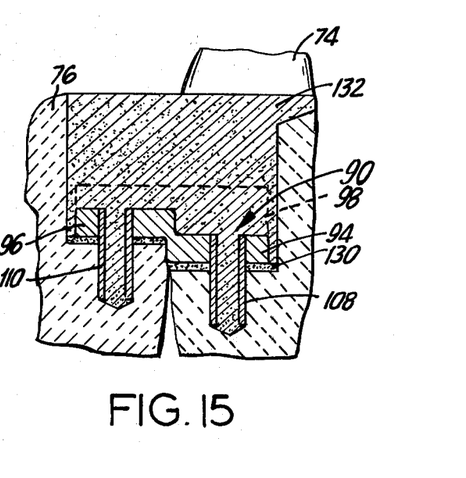
FIG. 15 is an elevational view, partially in cross section, similar to that shown in FIG. 14, showing the dental splinting device of FIGS. 10 and 11 permanently secured in the channel of the teeth with the channel being filled with suitable dental material.

The use of the dental splinting device of FIGS. 10 and 11 is similar to that heretofore described. Specifically, referring now to FIGS. 14 and 16, initially the tubular members 108, 110 are inserted into the openings 118, 120 provided therefor in the spacer block, and the spacer block is positioned in the channel. It should be noted, as shown in FIG. 14, that the lower base wall of the channel is also stepped with the base wall 122 of the channel 82 formed in the anterior tooth 74 being at a lower planar level than the channel base wall 124 formed in the posterior tooth 76. Accordingly, the stepped lower portion of the spacer block will be suitably received in the correspondingly stepped base wall of the channel.

The spacer block is temporarily retained in the channel by means of the temporary adhesive 126 and 128 as before. With the splinting device place within the spacer block, the tubular members 108, 110 are used as drill guides for the above mentioned drill 58 in order to drill the pilot holes into the teeth. The splinting device and the spacer block, together with the temporary adhesive, will then be removed and the above mentioned dental drill bit 64 will be used to form the bores using the pilot holes as lead holes. After the bores have been drilled, the stepped splinting device of FIGS. 10 and 11 will then be inserted into the bores, as is best shown in FIG. 13. A permanent adhesive 130 will be utilized to hold the splint in place and an inlay material 132 will be used to fill the channel and surround the splinting device.

It should be appreciated, that although the dental splinting device described in connection with FIGS. 1 and 2 is a universal type which can be used in conjunction with all of the anterior teeth, when using the stepped device of FIGS. 10 and 11 it will be necessary to provide right hand and left hand configuration. Specifically, in the upper left hand part of the mouth, the step from the posterior to the anterior teeth requires that the forward portion be at a lower level than the rearward portion. At the same time, it is also required that the longer wall of the J-shaped configuration be toward the labial surface. On the right hand upper portion of the mouth with respect to the labial surface, the right and left portions are reversed. Accordingly, separate splinting devices will be required for these two sections. The lower teeth, of course, can use the same two types as provided for the upper teeth, only they will be used in reverse.

Figure 16:
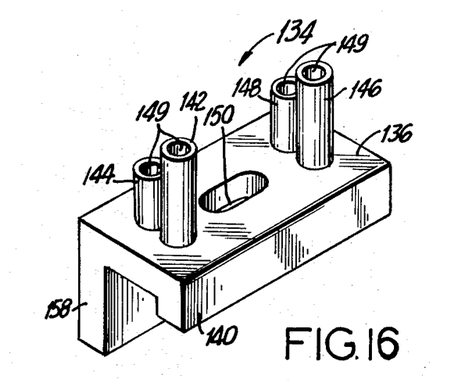
FIG. 16 is a perspective view illustrating another embodiment of the dental splinting device in accordance with the present invention.
Figure 17:
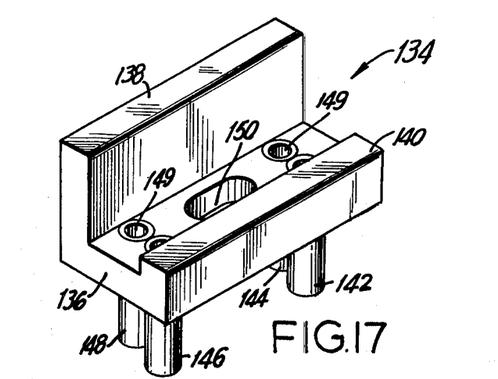
FIG. 17 is another perspective view illustrating the dental splinting device of FIG. 16, showing an opposite view thereof.

Referring now to FIGS. 16 and 17, there is shown yet a further embodiment of the dental splinting device, shown generally at 134. It should be appropriate that this device is similar to that shown in FIG. 1 with th exception that a pair of tubular members are utilized at each location with the tubular members of each pair being tangentially engaged against each other. More specifically, the dental splinting device includes a base wall 136, a downwardly depending rear wall 138 and a shorter downwardly depending front wall 40. Upwardly extending from the base wall 136 are a first pair of tubular members including the individual tubular members 142 and 144. The two tubular members have their centers lying on a line which is transverse with respect to the elongated direction of the bar like body member. The two tubular members are substantially tangential to each other. It is noted that the tubular member 144 adjacent the higher rear wall 138 is shorter in length than the other tubular member 142 of the same pair.

Spaced apart from the first pair of tubular members is provided a second pair of tubular members 146, 148 which are similar in construction to that previously described with respect to the first pair. The tubular members include axial holes 149 extending therethrough. Separating the two pairs of tubular members, and lying in an elongated direction, there is provided an elongated aperture 150. The aperture 150 can be utilized in a manner similar to the dimples in the previous embodiments in order to facilitate the location of a further bore which may be needed in the teeth. Additionally, during the course of a drilling operation the excess dentition material can be received within the aperture 150 in order to prevent accumulation and interference with the drilling operation. The aperture 150 can also receive a dental tool for picking up and positioning the splint.

Figure 18:
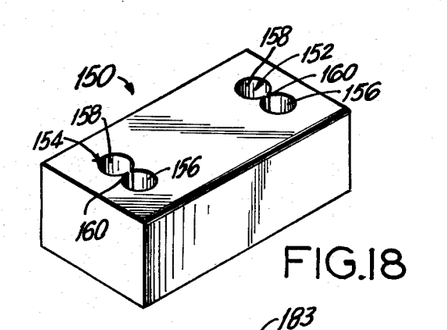
FIG. 18 is a perspective view showing the spacer block which is used in conjunction with the dental splinting device shown in FIGS. 16 and 17.

As shown in FIG. 18, there is provided a spacer block 150 similar to that provided in FIG. 3, except that the bore holes 152, 154 extending therethrough, provided to accommodate the pair of tubular members of the splinting device, are each formed as a pair of tangential bore holes 156, 158 which engage each other. It should be appreciated, that a portion of the interconnecting wall 160 between the two bore holes falls out as the two bore holes are formed due to the thinness thereof. Here again, the top and bottom surfaces are identical so that spacer block is always right-side up.

Figure 19:
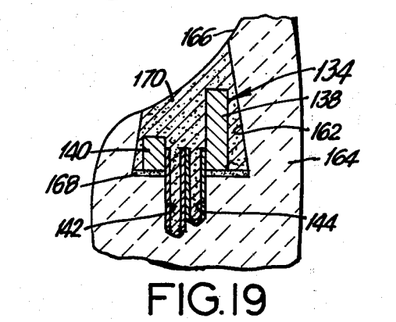
FIG. 19 is an elevational view, partially in cross section, illustrating the dental splinting device of FIGS. 16 and 17 permanently secured in the channel of the teeth with the channel being filled with suitable dental material.

The use of the splinting device shown in FIGS. 16-17 in conjunction with the block shown in FIG. 18, would be similar to that shown and described in connection with the first embodiment of the present invention. Specifically, a channel 162 would be formed in adjacent teeth, one of which is shown in FIG. 19 at 164 as being an anterior tooth with the channel being formed in the lingual surface 166. The spacer block would be temporarily placed at the bottom of the channel and held in place by a temporary adhesive. The tubular members would be inserted into the bore holes adapted to receive them in the spacer block. Pilot holes would then be drilled and both the spacer block and splinting device, together with the temporary adhesive, would be removed so that the pilot holes could be enlarged to form the bores in the teeth. The splinting device 134 is then inserted into the bores that are drilled such that the tubular members 142, 144 are inserted into the bores in the teeth. An adhesive 168 is used to secure the splinting member in the teeth, and dental filling material 170 is then inserted to securely retain the splint in place, as shown in FIG. 19.

The use of the pair of tubular members provides additional support and rigidity for the splint. Furthermore, it prevents the splint from breaking with the teeth and provides more holding action of the splint to the teeth. The tubular members 144, 148 of each pair are made shorter than the other tubular members 142, 146 in order not to engage or damage the pulp of the tooth.

Just as in connection with the first embodiment, a modification was provided in FIG. 10 in order to accomodate splinting between posterior and anterior teeth, then also a similar arrangement can be had in connection with the embodiment shown in FIG. 16. Specifically there is provided a stepped splint member so that a longer extending tubular member can be accommodated in the anterior teeth while a shorter tubular member is accommodated in the posterior teeth, such as arrangement being shown in FIGS. 20 and 21. A retaining splint, shown generally at 172, includes two adjacent sections 174, 176. The rear wall 178 is shown to have a substantially flat upper surface 180 while the front wall 182 has stepped sections corresponding to the stepped basewall. As a result, the section 174 has front and rear walls of equal height, whereas the section 176 has front and rear walls of different heights, so that the section 176 can be placed in the anterior teeth while the section 174 would be placed in the posterior teeth.

Figure 20:
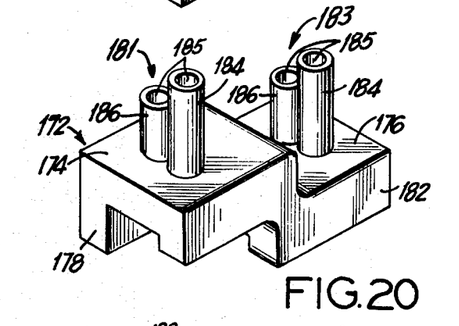
FIG. 20 is a perspective view illustrating yet a further embodiment of the dental splinting device in accordance with the present invention.
Figure 21:
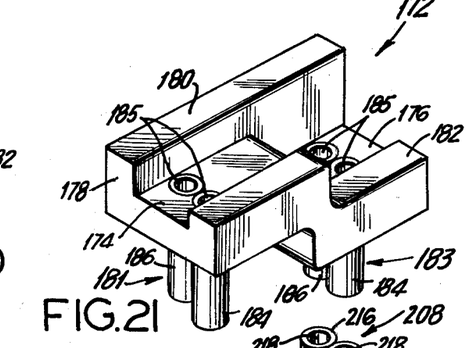
FIG. 21 is a perspective view illustrating the dental splinting device of FIG. 20 showing an opposite view of that shown in FIG. 20.

Upwardly extending from each of the base wall sections 174, 176 are a pair of tubular members 181, 183. Each of these pairs include two adjacent tubular members 184, 186 each of which has an axial opening 185 therethrough. It should be noted that the tubular member 184 has a greater length than does the tubular member 186, for the reason set forth above with respect to the pulp of the tooth.

Figure 22:
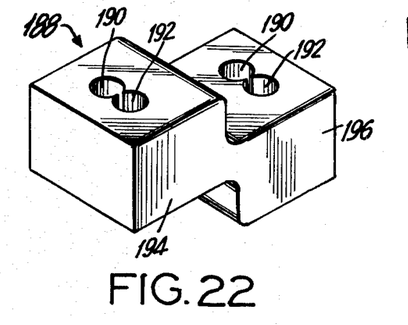
FIG. 22 is a perspective view of a spacer block for use in conjunction with the dental splinting device shown in FIGS. 20 and 21.

A spacer block similar to that heretofore shown in FIG. 12 is now provided as shown in FIG. 22, being shown generally at 188. The spacer block 188 includes a pair of adjacent engaging holes 190, 192 through each of its sections 194, 196 to receive the adjacent tubular members of the splinting device 172, the holes 190, 192 being similar to the holes 156, 158 in FIG. 18. All of the previous discussion in connection with the embodiment shown in FIGS. 10 through 15 also applied to the embodiment shown in FIGS. 20 through 22, where no further discussion thereof is thought necessary for a person skilled in the dental art.

Figure 23:
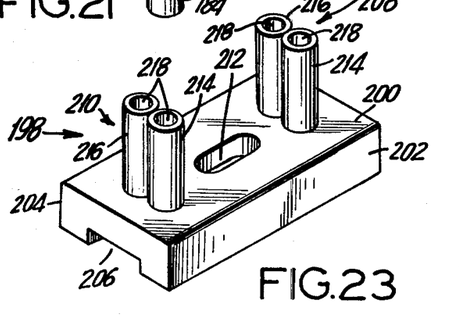
FIG. 23 is a perspective view illustrating yet another dental splinting device in accordance with the present invention.

Utilizing the same concept of providing the pair of tubular members, it is possible to provide a retaining splint 198 of the type shown in FIG. 23, which includes a basewall 200 substantially U-shaped in cross section with downwardly depending legs 202, 204 providing a channel 206 therebetween. The channel 206 would be utilized to receive the dental material during the drilling operation. Accordingly, the two legs 202, 204 are shown as being rather short. Upwardly extending from the basewall 200 are pairs of tubular members 208, 210 which are spaced apart with an elongated shaped aperture 212 spaced therebetween. Each of the pairs of tubular members includes substantially identical tubular members 214, 216 tangentially engaging each other. Axial openings 218 are provided through each of the tubular members.

The use of the splinting device 198 shown in FIG. 23 is similar to that heretofore explained in connection with the other splinting devices, however no spacer block would be needed, the splinting device 198 preferably being utilized in a posterior tooth. The use could then be similar to that described in the aforementioned partent application which describes a single tubular member, and described in the aforementioned U.S. Pat. No. 4,251,216 which describes double tubular members, without having any pairs of tangentially engaging tubular members as provided on the splinting device 198.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental splinting device comprising an elongated bar-like body member having a rear wall, a front wall, and a base wall interconnecting said front and rear walls, said front wall having a longitudinally extending portion shorter than said rear wall to thereby define a substantially J-shaped cross sectional configuration, at least one tubular member extending perpendicularly from said base wall for being received in a bore provided in a first tooth with said body member being disposed in a channel extending from the first tooth to at least one adjacent tooth, said tubular member including axial opening means extending therethrough for guiding a drill during formation of a pilot hole in the first tooth, the pilot hole functioning as a lead hole for the formation of said bore in the first tooth, and said body member including retaining means longitudinally spaced from said tubular member for securing said body member to the adjacent tooth when said body member is in a final position in the channel.

2. A dental splinting device as in claim 1, and further comprising a spacer block having at least one bore hole therethrough for receiving said tubular member during the formation of the pilot hole, said spacer block having a height proximating the extended distance of the tubular member from the base wall.

3. A dental splinting device as in claim 2, wherein said spacer block is of substantially rectangular configuration and has an outer surface area proximating the facing area of said base wall when said tubular member is received therein.

4. A dental splinting device as in claim 2, wherein said body member supports more than one tubular member, and wherein the bore holes in said spacer blocks are respectively aligned with the tubular members.

5. A dental splinting device as in claim 1, and further comprising a set of aligned dimples on opposite sides of said base wall to provide a reduced thickness in said base wall.

6. A dental splinting device as in claim 1, wherein said base wall comprises laterally adjacent sections vertically offset from each other to provide a stepped arrangement of the base wall.

7. A dental splinting device as in claim 6, wherein said front wall also comprises laterally adjacent sections commensurate with the sections of said base wall, and which are also vertically offset from each other to thereby provide a stepped arrangement of the front wall, said shorter front wall portion defining one of said front wall sections.

8. A dental splinting device as in claim 6, wherein the upper edge of the rear wall lies along a common plane which spans both sections of the base wall.

9. A dental splinting device as in claim 6, wherein there are two tubular members of substantially identical size, each tubular member extending from a respective section of the base wall to thereby provide a stepped arrangement of the tubular members.

10. A dental splinting device as in claim 9, and further comprising a spacer block having laterally adjacent sections vertically offset from each other to provide a stepped arrangement complementary to the base wall, a bore hole respectively extending through each section of the spacer block, each bore hole receiving a respective tubular member therein during the formation of the pilot hole, the height of each section of said spacer block corresponding to the extended distance of the tubular member which it receives.

11. A dental splinting device as in claim 2, wherein said body member supports at least one pair of tubular members, said tubular members of said pair tangentially engaging each other, and a corresponding pair of bore holes in said spacer blocks also tangentially connecting each other.

12. A dental splinting device as in claim 11, wherein the centers of each pair of tubular members lie on a respective line transverse to said body member, and the tubular member adjacent said rear wall extends a lesser distance from said base wall than the other tubular member of that pair.

13. A dental splinting device as in claim 12, wherein said body member supports more than one pair of tubular members, said pairs being longitudinally spaced apart from each other.

14. A dental splinting device as in claim 6, wherein a respective pair of tangentially engaging tubular members is provided on each section of the base wall to thereby provide a stepped arrangement of the pairs of tubular members.

15. A dental splinting device as in claim 14, wherein said tubular members of each pair have their centers lying on a respective line transverse to said body member, and the tubular member of each pair adjacent said rear wall extends a lesser distance from said base wall than the other tubular member of said pair.

16. A dental splinting device as in claim 1, and further comprising an elongated aperture through said base wall.

17. A dental splinting device comprising an elongated bar-like body member, at least one pair of tubular members extending perpendicularly from said body member and tangentially engaging each other, said pair of tubular members being received in correspondingly engaging bores provided in a first tooth with said body member being disposed in a channel extending from said first tooth to at least one adjacent tooth, each of said tubular members respectively including an axial opening means extending therethrough for guiding a drill during formation of a pilot hole in the first tooth, the pilot holes functioning as lead holes for the formation of said bores in said first tooth, and said body member including retaining means longitudinally spaced from said pair of tubular members for securing said body member to the adjacent tooth when said body member is in a final position in the channel.

18. A dental splinting device as in claim 17, wherein said body member comprises a base wall and depending front and rear walls to thereby define a substantially U-shaped cross sectional configuration.

19. A dental splinting device as in claim 17, wherein said body member includes laterally adjacent sections vertically offset from each other to provide a stepped arrangement of the base wall.

20. A dental splinting device as in claim 17, wherein said body member comprises a rear wall, a shortened front wall, and a base wall interconnecting said front and said rear walls to thereby define a substantially J-shaped cross sectional configuration.

21. A method for reinforcing dentition comprising:
forming a channel in a first tooth and extending said channel to at least one adjacent tooth;
temporarily disposing a spacer block having at least one bore hole therein, in said channel across said first and second teeth;
inserting a dental splinting member having at least one tubular member into said spacer block with the tubular member of said splinting member being received within the bore hole of the spacer block and being disposed on said first tooth;
drilling a pilot hole in said first tooth by using an axial opening through said tubular member as a guide for a first drill performing said drilling;
removing said spacer and said splinting member from said channel;
enlarging said pilot hole with a second drill to form a bore in said first tooth with said pilot hole functioning as a lead hole for said second drill;
repositioning and securing said splinting member in said channel with said tubular member disposed in said bore in said first tooth and with means securing said splint in said second tooth; and
filling said channel and covering said splinting member with a dental material.

22. A method according to claim 21, wherein said means for securing said splint and second tooth is a second tubular member disposed on said splinting member, and wherein said spacer block includes a second bore hole for receiving said second tubular member, said bore holes of said spacer block being aligned with said tubular members, said method further including disposing said second tubular member in said second bore hole of said spacer block, drilling a second pilot hole in said second tooth through an axial opening in said second tubular member, enlarging said second pilot hole to form a second bore in said second tooth after said splint is removed from said channel, and disposing said second tubular member in said second bore of said second tooth when said splint is repositioned in said channel.

* * * * *